US00PP13696P29

(12) United States Plant Patent
Heims

(10) Patent No.: US PP13,696 P2
(45) Date of Patent: Apr. 1, 2003

(54) TIARELLA PLANT NAMED 'SEAFOAM'

(75) Inventor: Daniel M. Heims, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 10/079,439

(22) Filed: Feb. 19, 2002

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette Para
(74) *Attorney, Agent, or Firm*—Klarquist Sparkman LLP

(57) ABSTRACT

A new and distinct hybrid of Tiarella characterized a distinct leaf form and coloration.

2 Drawing Sheets

Botanical classification: Tiarella hybrid.
Variety denomination: 'Seafoam'.

BACKGROUND OF THE INVENTION

The present invention relates to a new and distinct cultivar of a hardy herbaceous perennial of the genus Tiarella, and known by the cultivar name 'Seafoam'. The genus Tiarella is a member of the family Saxifragaceae.

The new cultivar originated as a cross between unknown parents. This new Tiarella was one of many seedlings grown from select interspecific hybrids and species that were mass pollinated in the greenhouse in Canby, Oreg. From observation of the characteristics exhibited by the instant plant, it is most likely an interspecific hybrid. As such no species designations are given.

The new variety has been reproduced only by asexual propagation (division and micropropagation). Each of the progeny exhibits identical characteristics to the original plant.

SUMMARY OF THE INVENTION

This plant is characterized by the following:

1. Small leaves and compact habit.
2. Strong, feather-like dark pattern following veins.
3. Many flowering stems.
4. White flower color.
5. Excellent vigor.

The new variety has been reproduced only by asexual propagation (division and micropropagation). Each of the progeny exhibits identical characteristics to the original plant. Asexual propagation by division and micropropagation using standard techniques with terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
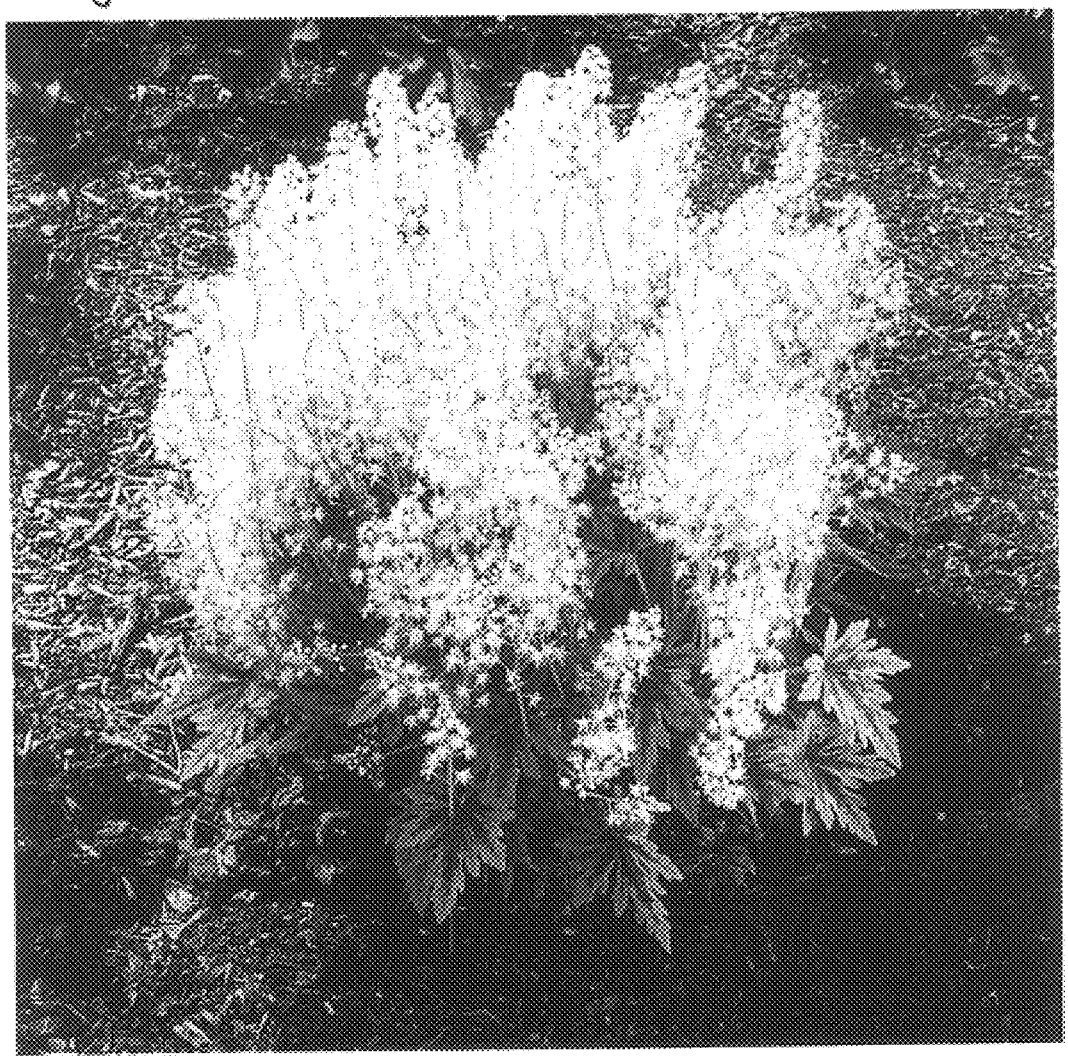
FIG. 1 is a picture of a one-and a half year old Tiarella 'Seafoam' in bloom in the garden on a sunny day in Canby, Oreg.
Figure 2:
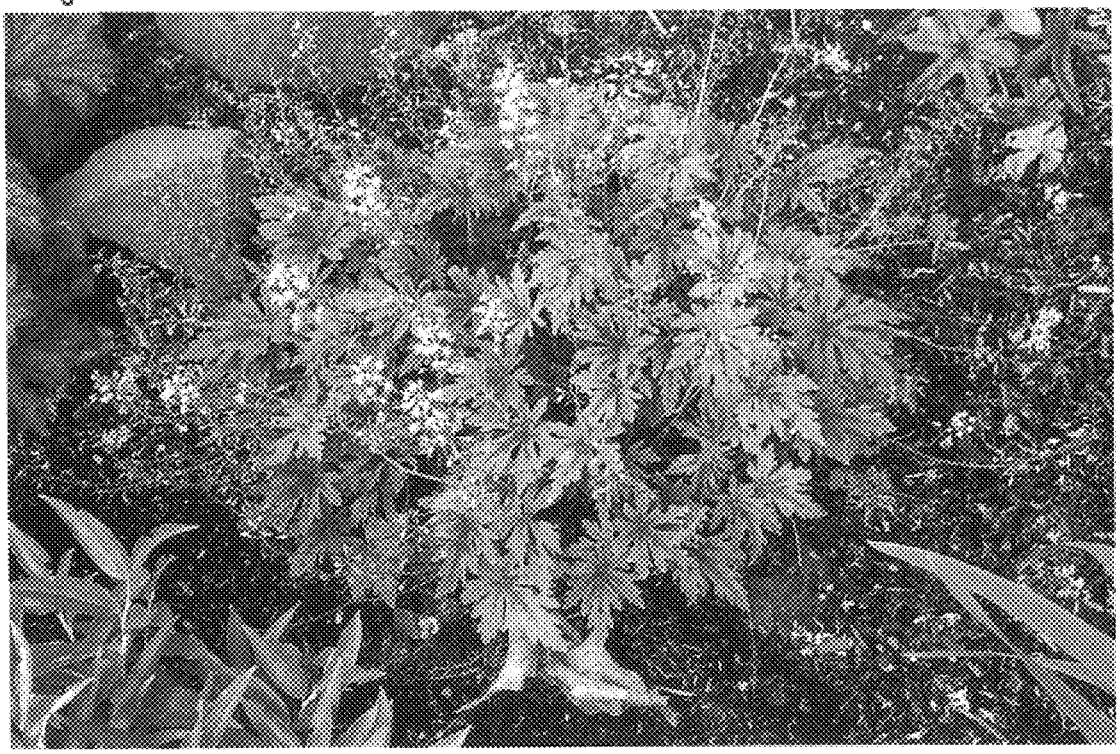
FIG. 2 shows a 2-year-old plant near the end of its bloom period on an overcast day.

The following is a detailed description of the new Tiarella hybrid based on observations of two-year-old plants grown in three-gallon pots in Canby, Oreg. The color descriptions are all based on The Royal Horticultural Society Colour Chart.

Botanical name: Tiarella hybrid.
Cultivar name: 'Seafoam'.
Plant:
- *Type.*—Herbaceous perennial.
- *Hardiness.*—USDA Zones 5 to 9.
- *Form.*—Basal clump.
- *Size.*—35 cm. wide and 17 cm. high.

Foliage:
- *Type.*—Simple.
- *Arrangement.*—Rosette.
- *Shape.*—Ovate in outline.
- *Lobing.*—Deeply 5 parted with terminal lobe about 2 times as long, and with each lobe irregularly lobed.
- *Margins.*—Incised and crenate.
- *Venation.*—Palmate.
- *Apex.*—Mucronulate.
- *Base.*—Cordate.
- *Blade length.*—Variable, 6.5 to 11.5 cm.
- *Blade width.*—Variable, 4.5 to 9.5 cm.
- *Texture.*—Rough.
- *Aspect.*—Matte.
- *Surface.*—Hirsute top and bottom.
- *Petiole length.*—Variable, 7.5 to 18 cm.
- *Petiole texture.*—Strongly pubescent.
- *Petiole color.*—Yellow Green 152A in spring or low light. Brown 200A at the lower ⅔ in summer.
- *Leaf color.*—From Yellow Green 146A in spring to Yellow Green 147A in summer with Greyed Purple 183A along main veins and filling out to ⅔ of leaf blade. In winter the leaves turn browner, Greyed Orange 166, with some rose pink highlights, Greyed Purple 184A. The dark pattern turns dark brown, Brown 200A.

Inflorescence:
- *Type.*—Raceme.
- *Flower number.*—40 per raceme.

*Bloom period.*—April to May with sporadic rebloom throughout the summer and fall.

*Peduncle.*—With 1 leaf bract, branching 1 to 2 times. Height — 35 cm. Width — 2 mm. at the widest point. Color — Yellow Green 151A with Greyed Red 183B. Texture — Hispid.

*Pedicel.*—Length — 0.8 to 1 cm. Texture — Puberulent. Color — Yellow Green 151A blushed with Greyed Red 182B.

*Bloom time.*—April to May and sporadic bloom through the summer.

Flower bud:

*Size.*—0.4 cm long and 0.35 cm wide.

*Description.*—Ovoid, downfacing until open.

*Color.*—Creamy gold, Yellow Orange 16D.

Flower:

*Type.*—Perfect, actinomorphic, sepals petaloid.

*Shape.*—Rotate.

*Petal and sepal number.*—5 petals, 5 fused sepals.

*Flower size.*—0.9 to 1.2 cm. wide and 0.5 cm. deep including stamens.

*Petal shape.*—Lanceolate with a clawed base.

*Petal size.*—0.6 cm long and 0.1 cm. wide.

*Petal color.*—White 155A.

*Calyx.*—Petaloid, parted almost to the base.

*Calyx size.*—1.1 cm. wide and 0.4 cm. deep.

*Calyx color.*—White 155A.

*Stamens.*—10, conspicuously exerted.

*Filaments.*—White 155A, 0.35 cm long.

*Anthers undehisced.*—Yellow 6B.

*Pollen color.*—Yellow 6A.

*Pistil.*—White 155A.

*Fragrance.*—None.

Fruit:

*Type.*—A one-celled capsule, beak-like, composed of two unequal parts.

*Size.*—0.8 cm long.

*Color.*—Brown 200B.

Seeds:

*Color.*—Black 202A.

*Shape.*—Minute, oval, 1 mm long.

*Fertility.*—Fertile.

Disease resistance: This new hybrid shows good mildew tolerance, the main problem for Tiarella.

COMPARISONS WITH SIMILAR TIARELLA

Compared with Tiarella 'Black Velvet' (U.S. Plant Pat. No. 12,348), Tiarella 'Seafoam' has more jagged and more divided leaves with narrower divisions. It also has gold buds rather than pink buds.

Compared with Tiarella 'Pink Skyrocket' (U.S. Plant patent application Ser. No. 09/990,638) Tiarella 'Seafoam' has more divided leaves and white flowers with gold buds rather than pink flowers and pink buds.

I claim:

1. A new and distinct hybrid of Tiarella plant substantially as shown and described, characterized by a distinct leaf form and coloration.

* * * * *